United States Patent [19]

Maerkl et al.

[11] Patent Number: 4,777,284

[45] Date of Patent: Oct. 11, 1988

[54] CONTINUOUS PREPARATION OF CARBALKOXY-CONTAINING ALIPHATIC COMPOUNDS

[75] Inventors: Robert Maerkl, Fussgoenheim; Werner Bertleff, Viernheim; Gebhard Kuehn, Ludwigshafen; Paul Panitz, Worms; Peter Stops, Altrip; Rudolf Kummer, Frankenthal; Guenter Schuch, Ludwigshafen, all of Fed. Rep. of Germany

[73] Assignee: BASF Aktengesellschaft, Fed. Rep. of Germany

[21] Appl. No.: 116,877

[22] Filed: Nov. 5, 1987

[30] Foreign Application Priority Data

Nov. 8, 1986 [DE] Fed. Rep. of Germany .... 3638219.1

[51] Int. Cl.$^4$ .............................................. C07C 67/38
[52] U.S. Cl. .................... 560/204; 560/190; 560/207; 560/233
[58] Field of Search ................ 560/190, 204, 207, 233

[56] References Cited

FOREIGN PATENT DOCUMENTS 1618156  5/1967  Fed. Rep. of Germany .

Primary Examiner—Werren B. Lone
Assistant Examiner—Vera C. Clarke
Attorney, Agent, or Firm—Keil & Weinkauf

[57] ABSTRACT

Carbalkoxy-containing aliphatic compounds are prepared continuously by reacting an olefinically unsaturated aliphatic compound with carbon monoxide and an alkanol in the presence of a cobalt carbonyl catalyst and a tertiary nitrogen base at from 80° to 200° C. and under from 100 to 1,200 bar by an improved process in which carbon monoxide is circulated, and a carbon dioxide content of from 0.1 to 2% by volume is maintained in the carbon monoxide fed to the reaction.

6 Claims, No Drawings

CONTINUOUS PREPARATION OF CARBALKOXY-CONTAINING ALIPHATIC COMPOUNDS

The present invention relates to a process for the continuous preparation of carbalkoxy-containing aliphatic compounds by reacting an olefinically unsaturated aliphatic compound with carbon monoxide and an alkanol in the presence of a cobalt carbonyl catalyst and a tertiary nitrogen base.

German Laid-Open Application DOS No. 1,618,156 discloses a process in which olefins or alkenecarboxylates are carbalkoxylated by reaction with carbon monoxide and alkanols in the presence of cobalt carbonyl catalysts and heterocyclic aromatic tertiary nitrogen bases. When the process is carried out industrially, the carbon monoxide employed in excess is reused, advantageously under reaction pressure. This results in deposition of cobalt oxalate and a reduction in the reaction rate in the carbalkoxulation reaction.

It is an object of the present invention to provide a process for the preparation of a carbalkoxy-containing aliphatic compound by carbalkoxylation of an olefinically unsaturated aliphatic compound, in which deposition of cobalt oxalate is avoided and there is little or no adverse effect on the reaction rate.

We have found that this object is achieved by a process for the preparation of a carbalkoxy-containing aliphatic compounds by reacting an olefinically unsaturated aliphatic compound with carbon monoxide and an alkanol in the presence of a cobalt carbonyl catalyst and a tertiary nitrogen base at from 80° to 200° C. and under from 100 to 1,200 bar, wherein carbon monoxide is circulated, and a carbon dioxide content of from 0.1 to 2.0% by volume is maintained in the carbon monoxide fed to the reaction.

The novel process has the advantage that the reaction rate during carbalkoxylation is not adversely affected and furthermore deposition of the cobalt oxalate is avoided.

Apart from carbalkoxy groups as substituents, the olefinically unsaturated compounds used as starting materials generally have a hydrocarbon structure. Preferred starting materials are olefins and diolefins of 4 to 16 carbon atoms which may furthermore be substituted by carbalkoxy of 2 to 5 carbon atoms, in particular alphaolefins of 4 to 10 carbon atoms or esters of alkenecarboxylic acids of 4 to 11 carbon atoms. Examples of suitable starting materials are isobutylene, butene, but-1-ene, oct-2-ene, oct-1-ene, diisobutylene, hex-1-ene, butadiene, hexadiene, undecylenoates and methyl pent-3-enoates, in particular butadiene and butadiene-containing C$_4$ cuts, for example those containing from 30 to 70% by weight of butadiene.

Preferred products are accordingly alkanecarboxylates, alkenecarboxylates and alkanedicarboxylates.

Suitable alkanols advantageously have from 1 to 6, in particular from 1 to 4, carbon atoms, examples being methanol, ethanol, isopropanol, butanol and hexanol. Methanol is particularly preferred.

As a rule, the alkanols are used in excess. Advantageously, from 1.5 to 10, in particular from 2 to 5, moles of alkanol are employed per mole of olefinically unsaturated compound.

The reaction is carried out at from 80° to 200° C., particularly good results being obtained at from 100° to 180° C. Furthermore, a pressure of from 100 to 1,200, in particular from 150 to 900, bar is maintained during the reaction.

Carbon monoxide is advantageously used in excess, for example in from 1.5 to 10 times the stoichiometric amount. Carbon monoxide is continuously circulated. According to the invention, the carbon dioxide content of the carbon monoxide fed to the reaction (mixture of recycled gas and fresh carbon monoxide) is from 0.1 to 2.0, in particular from 0.5 to 1.8, % by volume.

The cobalt carbonyl catalysts used may be produced in situ from cobalt salts, for example cobalt salts of fatty acids, such as formate, acetate, propionate or butyrate. The catalyst is advantageously introduced in the form of cobalt carbonyl itself. In particular, it has proven useful if cobalt carbonyl catalyst dissolved in the olefinically unsaturated starting compound is introduced into the reaction mixture. Such a solution is obtained, for example, by reacting an aqueous solution of a cobalt salt of a fatty acid with a mixture of carbon monoxide and hydrogen in the presence of active carbon at from 100° to 170° C. and under from 100 to 400 bar. The resulting cobalt carbonyl is then extracted from the aqueous solution with the olefinically unsaturated compound.

The reaction is carried out in the presence of a tertiary nitrogen base, in particular a heterocyclic aromatic tertiary nitrogen base, advantageously having a pK$_a$ of from 6 to 9.

Examples of suitable nitrogen bases are 3-methylpyridine (pK$_a$ 6.0), 4-methylpyridine (pK$_a$ 6.0), 2,3-dimethylpyridine (pK$_a$ 6.6), 2,4-dimethylpyridine (pK$_a$ 7.0) and 3,5-dimethylpyridine (pK$_a$ 6.2). 3-methylpyridine and 4-methylpyridine and mixtures thereof have become particularly important industrially. It has proven especially advantageous to use from 2 to 25 moles of the abovementioned nitrogen bases per mole of cobalt carbonyl catalyst.

The process according to the invention is carried out, for example, by continuously feeding olefinically unsaturated compounds, alkanols, cobalt carbonyl catalysts, heterocyclic aromatic tertiary nitrogen bases and carbon monoxide in the stated ratios into one or more stainless steel high-pressure vessels in which good mixing is ensured, for example two loop reactors connected in series, and maintaining the reaction mixture at the stated temperature and the stated pressure. Reaction mixture is removed at the rate at which the starting materials are fed in, and carbon monoxide is separated off and fresh carbon monoxide added to the reaction mixture. The remaining reaction mixture is let down and then worked up by separating off the Cobalt catalyst, for example by treatment in an aqueous acidic medium with a gas containing molecular hydrogen, removing the cobalt salt solution and distilling the organic phase. The carboxylates prepared by the process of the invention are useful as starting materials for fiber raw materials or as plasticizers for high polymers.

The Examples which follow illustrate the process according to the invention. Parts by weight bear the same relation to parts by volume as that of the kilogram to the liter.

EXAMPLE 1 a. 33 parts by weight/hour of a C$_4$ cut containing 40% (m/m) of buta-1,3-diene, 27 parts by weight/hour of 3-methylpyridine, 11 parts by weight/hour of methanol, 1 part by weight/hour of cobalt in the form of a cobalt carbonyl compound and 28 parts by weight/hour of a gas mixture composed of 83.5% of carbon monoxide,
1.3% of carbon dioxide,
2.6% of nitrogen and
12.5% of butenes are fed from below into a high pressure vessel having a capacity of 100 parts by volume.

The carbonylation takes place at 135° C. and under 650 bar. The product taken off at the top of the high pressure vessel is let down, and the circulating gas removed is recycled to the synthesis. The excess $C_4$ hydrocarbons are then separated off. They contain 1,000 ppm of butadiene, corresponding to a conversion of 99.9%.

b. Methanol, methyl pent-3-enoate and the major part of the 3-methylpyridine are distilled off from the discharged mixture under reduced pressure, in order to protect the catalyst.

c. The resulting bottom product of the distillation is diluted with methyl pent-3-enoate and methanol. 16 parts by weight of carbon monoxide are added to this reaction solution, which contains 55 parts by weight of methyl pent-3-enoate, 46 parts by weight of 3-methylpyridine, 23 parts by weight of methanol and 1 part by weight of cobalt in the form of a cobalt-carbonyl compound, and the mixture is fed continuously from below into a further high pressure vessel. Carbonylation is carried out at 165° C. and under 150 bar. The conversion of the methyl pent-3-enoate is 72%, and the selectivity with respect to dimethyl adipate is 79%. The product removed at the top of the high pressure vessel is let down, excess carbon monoxide escaping in gaseous form. It contains 5% (m/m) of carbon dioxide. This gas stream is recycled to the first carbonylation stage and mixed with fresh carbon monoxide, so that the carbon dioxide content of the mixture fed to the first reaction stage is 1.3% by volume.

EXAMPLE 2 (COMPARATIVE EXAMPLE)

Dimethyl adipate is prepared continuously in a two-stage procedure from butadiene, carbon monoxide and methanol, as described in Example 1.

However, the waste gas in stage 1c) contains 15% (m/m) of carbon dioxide. Where the amount of fresh carbon monoxide is unchanged, this leads to a carbon dioxide content of 2.7% (m/m) in the mixture fed to stage 1a). The conversion in stage 1a) decreases to 99.6%. When the interior of the high pressure vessels is inspected, a deposit is found; this is identified as cobalt oxalate by analysis.

We claim:

1. In an improved process for the continuous preparation of a carbalkoxy-containing aliphatic compound by reacting an olefinically unsaturated aliphatic compound with carbon monoxide and an alkanol in the presence of a cobalt carbonyl catalyst and a tertiary nitrogen base at from 80° to 200° C. and under from 100 to 1,200 bar, the improvement that carbon monoxide is circulated, and a carbon dioxide content of from 0.1 to 2.0% by volume is maintained in the carbon monoxide fed to the reaction.

2. A process as claimed in claim 1, wherein the heterocyclic aromatic tertiary nitrogen base having a $pK_a$ of from 6 to 9 is used.

3. A process as claimed in claim 1, wherein an alpha-olefin of 4 to 10 carbon atoms is used as a starting material.

4. A process as claimed in claim 1, wherein butadiene or a butadiene-containing $C_4$ cut is used.

5. A process as claimed in claim 1, wherein an ester of an alkenecarboxylic acid of 4 to 11 carbon atoms is used as a starting material.

6. A process as claimed in claim 1, wherein 3-methylpyridine, 4-methylpyridine or a mixture thereof is present.

* * * * *